United States Patent
Armstrong (10) Patent No.: US 8,764,791 B2
(45) Date of Patent: Jul. 1, 2014

(54) IMPLANTABLE GRAFT TO CLOSE A FISTULA

(75) Inventor: David N. Armstrong, Atlanta, GA (US)

(73) Assignee: Cook Medical Technologies LLC, Bloomington, IN (US)

( * ) Notice: Subject to any disclaimer, the term of this patent is extended or adjusted under 35 U.S.C. 154(b) by 823 days.

(21) Appl. No.: 11/807,801

(22) Filed: May 30, 2007

(65) Prior Publication Data

US 2007/0233278 A1    Oct. 4, 2007

Related U.S. Application Data (62) Division of application No. 11/040,996, filed on Jan. 21, 2005, now abandoned.

(60) Provisional application No. 60/538,365, filed on Jan. 21, 2004.

(51) Int. Cl.
*A61B 17/10* (2006.01)
*A61D 1/00* (2006.01)

(52) U.S. Cl.
USPC ........................................ 606/213; 623/23.72

(58) Field of Classification Search
USPC ......... 606/151, 153, 213, 214, 215; 623/1.23, 623/23.64, 23.72; 128/898
See application file for complete search history.

(56) References Cited

U.S. PATENT DOCUMENTS

| | | | |
|---|---|---|---|
| 1,887,526 A * | 11/1932 | Spielberg et al. | 604/287 |
| 2,127,903 A | 8/1938 | Bowen | |
| 3,958,556 A * | 5/1976 | Schenk | 600/32 |
| 3,996,921 A | 12/1976 | Neuwirth | |
| 4,209,009 A * | 6/1980 | Hennig | 600/30 |
| 4,511,653 A | 4/1985 | Play | |
| 4,693,236 A * | 9/1987 | Leprevost | 600/32 |
| 4,902,508 A | 2/1990 | Badylak et al. | |
| 4,956,178 A | 9/1990 | Badylak et al. | |
| 4,981,465 A * | 1/1991 | Ballan et al. | 600/32 |
| 5,275,826 A | 1/1994 | Badylak et al. | |
| 5,281,422 A | 1/1994 | Badylak et al. | |
| 5,330,503 A | 7/1994 | Yoon | |
| 5,345,948 A | 9/1994 | O'Donnell, Jr. | |
| 5,374,261 A | 12/1994 | Yoon | |
| RE34,866 E | 2/1995 | Kensey et al. | |

(Continued)

FOREIGN PATENT DOCUMENTS

| | | |
|---|---|---|
| EP | 0 894 474 A1 | 2/1999 |
| RU | 2180529 | 8/1999 |

(Continued)

OTHER PUBLICATIONS

Sentovic Stephen M., Fibrin glue for anal fistulas. Dis Colon Rectum 2003;46:498-502.

(Continued)

*Primary Examiner* — Dianne Dornbucsh
(74) *Attorney, Agent, or Firm* — Brinks Gilson & Lione (57) ABSTRACT

An implantable graft, which may be inserted into a fistula tract to occlude the primary opening of the fistula, is provided. The graft may have a curved, generally conical shape with a trumpet-like head end that continuously tapers to a smaller tail end. The graft may be an integral unit made of a single material, such as a heterograft material. Methods of closing single and multiple fistulae are also provided.

20 Claims, 3 Drawing Sheets

(56) References Cited

U.S. PATENT DOCUMENTS

| | | | |
|---|---|---|---|
| 5,514,158 | A | 5/1996 | Kanesaka |
| 5,516,533 | A | 5/1996 | Badylak et al. |
| 5,522,840 | A | 6/1996 | Krajicek |
| 5,554,389 | A | 9/1996 | Badylak et al. |
| 5,562,599 | A * | 10/1996 | Beyschlag ............... 600/29 |
| 5,584,827 | A | 12/1996 | Korteweg et al. |
| 5,620,461 | A | 4/1997 | Muijs Van De Moer |
| 5,628,762 | A | 5/1997 | Al-Tameem |
| 5,643,305 | A | 7/1997 | Al-Tameem |
| 5,713,891 | A * | 2/1998 | Poppas ................... 606/2 |
| 5,733,337 | A | 3/1998 | Carr, Jr. et al. |
| 5,752,974 | A | 5/1998 | Rhee et al. |
| 5,755,791 | A | 5/1998 | Whitson et al. |
| 5,846,183 | A | 12/1998 | Chilcoat |
| 5,860,978 | A | 1/1999 | McDevitt et al. |
| 5,947,994 | A | 9/1999 | Louw et al. |
| 5,955,110 | A | 9/1999 | Patel et al. |
| 5,993,844 | A | 11/1999 | Abraham et al. |
| 5,997,575 | A | 12/1999 | Whitson et al. |
| 6,090,996 | A | 7/2000 | Li |
| 6,099,567 | A | 8/2000 | Badylak et al. |
| 6,149,581 | A | 11/2000 | Klingenstein |
| 6,203,563 | B1 * | 3/2001 | Fernandez ............ 606/215 |
| 6,206,931 | B1 | 3/2001 | Cook et al. |
| 6,270,515 | B1 | 8/2001 | Linden |
| 6,296,632 | B1 | 10/2001 | Lüscher et al. |
| 6,315,787 | B1 | 11/2001 | Tsugita et al. |
| 6,331,319 | B1 | 12/2001 | Badylak et al. |
| 6,464,999 | B1 * | 10/2002 | Huo et al. ............. 424/422 |
| 6,475,232 | B1 | 11/2002 | Babbs et al. |
| 6,569,081 | B1 * | 5/2003 | Nielsen et al. ........... 600/32 |
| 6,638,312 | B2 | 10/2003 | Plouhar et al. |
| 6,666,892 | B2 | 12/2003 | Hiles |
| 6,688,312 | B2 * | 2/2004 | Yeretsian ............. 128/898 |
| 6,800,056 | B2 | 10/2004 | Tartaglia et al. |
| 7,485,087 | B2 * | 2/2009 | Burgard ............... 600/32 |
| 7,645,229 | B2 * | 1/2010 | Armstrong ............ 600/104 |
| 7,765,007 | B2 * | 7/2010 | Martino et al. ........ 607/40 |
| 2002/0198517 | A1 | 12/2002 | Alfano et al. ........... 606/8 |
| 2003/0013989 | A1 | 1/2003 | Obermiller et al. |
| 2003/0051735 | A1 * | 3/2003 | Pavcnik et al. ........ 128/831 |
| 2004/0064017 | A1 | 4/2004 | Cappiello et al. |
| 2004/0069312 | A1 * | 4/2004 | Ohmi ................. 128/898 |
| 2004/0260257 | A1 * | 12/2004 | Ciok et al. ............ 604/332 |
| 2005/0013844 | A1 | 1/2005 | Hadlock et al. |
| 2005/0049626 | A1 * | 3/2005 | Burgard ............... 606/191 |
| 2005/0070759 | A1 * | 3/2005 | Armstrong ........... 600/105 |
| 2005/0155608 | A1 | 7/2005 | Pavcnik et al. |
| 2005/0159776 | A1 * | 7/2005 | Armstrong ............ 606/213 |
| 2005/0182495 | A1 * | 8/2005 | Perrone .............. 623/23.72 |
| 2006/0015142 | A1 * | 1/2006 | Malazgirt ............ 606/213 |
| 2006/0058576 | A1 * | 3/2006 | Davies et al. ........... 600/32 |
| 2006/0074447 | A2 * | 4/2006 | Armstrong ............ 606/213 |
| 2007/0129757 | A1 * | 6/2007 | Armstrong ............ 606/213 |
| 2008/0004657 | A1 * | 1/2008 | Obermiller et al. ...... 606/213 |
| 2008/0051831 | A1 * | 2/2008 | Deal et al. ............ 606/213 |
| 2009/0012558 | A1 * | 1/2009 | Chen et al. ........... 606/213 |
| 2009/0054927 | A1 * | 2/2009 | Agnew ............... 606/213 |
| 2009/0125119 | A1 * | 5/2009 | Obermiller et al. ....... 623/23.65 |
| 2009/0326577 | A1 * | 12/2009 | Johnson et al. ........ 606/213 |

FOREIGN PATENT DOCUMENTS

| | | | |
|---|---|---|---|
| SU | 1718837 | 3/1992 | |
| WO | WO 93/16658 | 9/1993 | |
| WO | WO 97/41778 | 11/1997 | |
| WO | WO 98/01088 | 1/1998 | |
| WO | WO 98/22158 | 5/1998 | |
| WO | WO 98/25637 | 6/1998 | |
| WO | WO 00/74576 | * 12/2000 | ........ A61B 17/12 |
| WO | WO 00/74576 A1 | 12/2000 | |
| WO | WO 02/074192 A2 | 2/2002 | |
| WO | WO 02/062234 A2 | 8/2002 | |
| WO | WO 03/002165 | 1/2003 | |
| WO | WO 2004/103187 | 12/2004 | |
| WO | WO 2005/020823 | 3/2005 | |
| WO | WO 2005/020847 | 3/2005 | |
| WO | WO 2005/030035 | 4/2005 | |
| WO | WO 2005/053617 A2 | 6/2005 | |
| WO | WO 2005/070489 | 8/2005 | |
| WO | WO 2006/119256 A | 11/2006 | |

OTHER PUBLICATIONS

Lindsey I, Smilgin-Humphreys MM, Cunningham C, Mortensen NJM, George B. A randomized, controlled trial of fibrin glue vs conventional treatment for anal fistula. Dis Colon Rectum 2002;45:1608-15.

Athanasiadis S, Helmes C, Yazigi R, Köhler A. The direct closure of the internal fistula opening without advancement flap for transsphincteric fistulas-in-ano. Dis Colon Rectum 2004;47:1174-80.

Excision of anal fistula with closure of the internal opening. Gustafsson U Dis Colon Rectum 2002;45:1672-1678.

Practice parameters for treatment of fistula in ano. The Standards Practice Task Force of the American Society of Colon and Rectal Surgeons, Dis Colon Rectum, pp. 1363-1372, Dec. 1996.

Practice parameters for treatment of fistula in ano—Supporting documentation. The Standards Practice Task Force of the American Society of Colon and Rectal Surgeons, Dis Colon Rectum, pp. 1361.

Gordon N. Buchanan, M.Sc., F.R.C.S., Clive I. Bartram, F.R.C.R., Robin K.S. Phillips, M.S., F.R.C.S., Stuart W.T. Gould, M.S., F.R.C. S., Steve Halligan, M.D., F.R.C.R., Tim A. Rackall, M.D., F.R.C.S., Paul Sibbons, Ph.D., Richard G. Cohen, M.D., F.R.C.S., Efficacy of Fibrin Sealant in the Management of Complex Anal Fistula, Dis Colon Rectum, pp. 1167-1174, Sep. 2003.

Julio Garcia-Aguilar, M.D., Ph.D., Cynthia S. Davey, M.S., Chap T. Le, Ph.D., Ann C. Lowry, M.D. and David A. Rothenberger, M.D., Patient satisfaction after surgical treatment for fistula-in-ano, Dis Colon Rectum, pp. 1206-1212, Sep. 2000.

Schouten WR, Zimmerman DDE, Meuwissen SGM, "General Introduction and Outline of Thesis," Nederlands Tijdschrift voor Geneeskunde, Jul. 2001, 145(29): 1398-1402; https://ep.eur.nl/retrieve/2688.01.pdf#search='fistulotomy'.

David J. Schultz et al., "Procine Small Intestine Submucosa as a Treatment for Enterocutaneous Fistulas", J Am. Coll. Surg. pp. 541-543 (2002).

J.R. Miklos et al., "Rectovaginal Fistula Repair Utilizing a Cadaveric Dermal Allograft" Int. Urogynecol. J. 10: pp. 405-406 (1999).

Search Report for PCT/2006/045890.

* cited by examiner

FIG. 4

IMPLANTABLE GRAFT TO CLOSE A FISTULA

RELATED APPLICATIONS

The present patent application is a division of U.S. patent application Ser. No. 11/040,996, filed Jan. 21, 2005 which claims the benefit of the filing date under 35 U.S.C. §119(e) of Provisional U.S. Patent Application Ser. No. 60/538,365, filed Jan. 21, 2004. The contents of both prior applications are hereby incorporated by reference.

FIELD OF THE INVENTION

A graft for occluding a fistula is provided. The graft may be pulled, tail first, into the fistula to completely occlude the fistula, thereby avoiding a surgical fistulotomy and its attendant complications.

BACKGROUND OF THE INVENTION

Fistulae occur commonly in man. Such fistulae may be congenital or may be caused by infection, inflammatory bowel disease (Crohn's disease), irradiation, trauma, childbirth, or surgery, for example.

Some fistulae occur between the vagina and the bladder (vesico-vaginal fistulae) or between the vagina and the urethra (urethro-vaginal fistulae). These fistulae may be caused by trauma during childbirth. Traditional surgery for these types of fistulae is complex and not very successful.

Other fistulae include, but are not limited to, tracheo-esophageal fistulae, gastro-cutaneous fistulae, and anorectal fistulae. For example, anorectal fistulae may occur between the anorectum and vagina (recto-vaginal fistulae), between the anorectum and bladder (recto-vesical fistulae), between the anorectum and urethra (recto-urethral fistulae), or between the anorectum and prostate (recto-prostatic fistulae). Anorectal fistulae may result from infection in the anal glands, which are located around the circumference of the distal anal canal forming an anatomic landmark known as the dentate line 1, shown in FIGS. 1 and 2. Approximately 20-39 such glands are found in man. Infection in an anal gland may result in an abscess, which then tracks through or around the sphincter muscles into the perianal region, where it drains either spontaneously or surgically. The resulting tract is known as a fistula. The inner opening of the fistula, usually located at the dentate line, is known as the primary opening 2. The outer (external) opening, located in the perianal skin, is known as the secondary opening 3.

Figure 1:
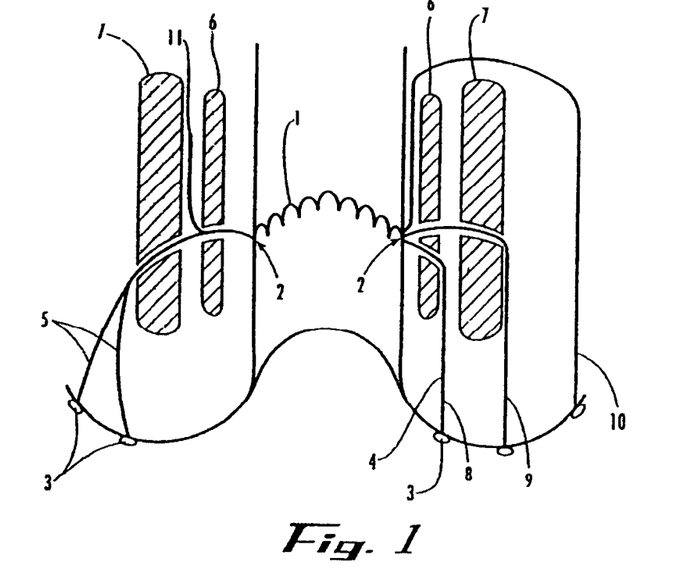
FIG. 1 shows several possible anatomic courses taken by various forms of anorectal fistula (longitudinal plane)
Figure 2:
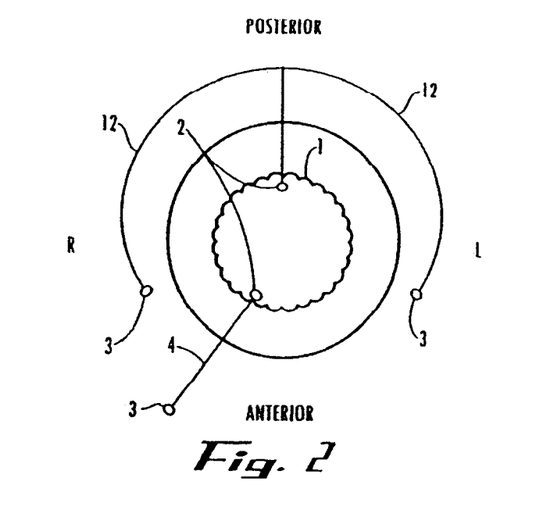
FIG. 2 shows a perineal view of a simple anorectal fistula and a horseshoe fistula.

FIGS. 1 and 2 show examples of the various paths that an anorectal fistula may take. These paths vary in complexity. Fistulae that take a straight line path from the primary opening 2 to the secondary opening 3 are known as simple fistulae 4. Fistula that contain multiple tracts ramifying from the primary opening 2 and have multiple secondary openings 3 are known as complex fistulae 5.

The anatomic path that an anorectal fistula takes is classified according to its relationship to the anal sphincter muscles 6, 7. The anal sphincter includes two concentric bands of muscle—the inner, or internal, sphincter 6 and the outer, or external, anal sphincter 7. Fistulae which pass between the two concentric anal sphincters are known as inter-sphincteric fistulae 8. Those which pass through both internal 6 and external 7 sphincters are known as trans-sphincteric fistulae 9, and those which pass above both sphincters are called supra-sphincteric fistulae 10. Fistulae resulting from Crohn's disease usually ignore these anatomic paths, and are known as extra-anatomic fistulae.

Many complex fistulae contain multiple tracts, some blind-ending 11 and others leading to multiple secondary openings 3. One of the most common and complex types of fistulae are known as horseshoe fistulae 12, as illustrated in FIG. 2. In this instance, the infection starts in the anal gland (the primary opening 2) and two fistulae pass circumferentially around the anal canal, forming a characteristic horseshoe configuration 12.

Surgical treatment of fistulae traditionally involves passing a fistula probe through the tract, in a blind manner, using only tactile sensation and experience to guide the probe. Having passed the probe through the fistula tract, the overlying tissue is surgically divided. This is known as a surgical fistulotomy. Because a variable amount of sphincter muscle is divided during the procedure, fistulotomy may result in impaired sphincter control or even incontinence.

Alternatively, the fistula tract may be surgically drained by inserting a narrow diameter rubber drain, known as a seton, through the tract. After the seton is passed through the fistula tract, it may be tied as a loop around the contained tissue and left for several weeks or months. This procedure is usually performed to drain infection from the area and to mature the fistula tract prior to a definitive closure or sealing procedure.

More recently, methods have evolved to inject sclerosant or sealant (collagen or fibrin glue) into the tract of the fistula. Such sealants are described in Rhee, U.S. Pat. No. 5,752,974, for example. The main drawback with these methods is that the glues have a liquid consistency and tend to run out of the fistula tract once the patient becomes ambulatory. In addition, failure rates of these methods are high (up to 86% failure). See Buchanan et al., *Efficacy of Fibrin Sealant in the Management of Complex Anal Fistula*, DIS COLON AND RECTUM Vol. 46, No. 9, 46:1167-1174 (September 2003). Usually, multiple injections of glue are required to close the fistula. In some instances, closure of a fistula using a sealant may be performed as a two-stage procedure, comprising a first-stage seton placement, followed by injection of the fibrin glue several weeks later. This procedure reduces residual infection and allows the fistula tract to "mature" prior to injecting a sealant. Injecting sealant or sclerosant into an unprepared or infected fistula as a one-stage procedure may cause a flare-up of the infection and even further abscess formation. Alternative methods and instruments, such as coring-out instruments (See, e.g., U.S. Pat. Nos. 5,628,762 and 5,643,305), simply make the fistula wider and more difficult to close.

An additional means of closing the primary opening is by surgically creating a flap of skin, which is drawn across the opening and sutured in place. This procedure (the endo-anal flap procedure) closes the primary opening, but is technically difficult to perform, is painful for the patient, and is associated with a high fistula recurrence rate.

An important step in successful closure of a fistula is accurate identification and closure of the primary opening. An accurate means of identifying the primary opening involves endoscopic visualization of the fistula tract (fistuloscopy), as disclosed in co-pending application Ser. No. 10/945,634 (Armstrong). Once the primary opening has been accurately identified, effective closure is necessary to prevent recurrence. The current invention comprises a graft that may be used to effectively plug or occlude the primary opening of the fistula tract.

SUMMARY OF THE INVENTION

One object of the present invention is to provide a new technique of minimally invasive fistula closure. Another object is to provide a technique that obviates the need for surgical fistulotomy and avoids surgical pain and the attendant complications of the procedure. Still another object of the invention is to provide an accurate and complete closure of a fistula, thereby preventing a recurrent or persistent fistula. Yet another object of the present invention is to provide a technique that involves no cutting of tissue, sphincter damage, or incontinence.

The present invention may be used in any type of fistula. For example, the claimed devices and methods may be used to plug or occlude tracheo-esophageal fistulae, gastro-cutaneous fistulae, anorectal fistulae, fistulae occurring between the vagina and the urethra or bladder, or fistulae occurring between any other two portions of the body.

In one embodiment of the present invention, a biocompatible graft having a curved, generally conical shape is provided. The graft may be used to plug, or occlude the primary opening of the fistula. Desirably, the graft is approximately 5 to 10 centimeters (2 to 4 inches) long and tapers continuously from a thicker, "trumpet-like" head to a thin filamentous tail. Desirably, the diameter of the head is approximately 5 to 10 millimeters and tapers to a diameter of 1 to 2 millimeters at its tail.

The graft of the present invention may be made of any suitable biological or synthetic materials. Desirably, the head and the tail are one continuous piece made of the same material. Suitable biological materials include, but are not limited to, cadaveric allografts from human donors or heterografts from animal tissues. Suitable synthetic materials include, but are not limited to, polygalactin, polydioxanone and polyglycolic acid. Desirably, the biological and/or synthetic material used in the graft of the present invention elicits little immunological reaction, has some inherent resistance to infection, and promotes tissue reconstruction (rather than complete absorption of the graft into the surrounding tissue), thereby occluding the fistula.

The graft of the present invention may be pulled into the fistula, tail first, through the primary opening, toward the secondary opening. In one embodiment, the graft is drawn into the fistula and the trumpet-like head end of the graft is gradually "wedged" into the primary opening in a manner similar to that of inserting a plug in a hole. The head and/or tail may be further secured by sutures or other suitable means, which may be formed as an integral part of the graft. A trumpet-like head allows the graft to be used for any diameter of primary opening. By applying adequate force to the graft during its insertion, the head of the graft fits snugly into the primary opening and conforms to the size of the primary opening. Multiple or composite grafts may be used for multiple or complex fistulae.

Additional features and advantages of the present invention will be apparent to one of ordinary skill in the art from the drawings and detailed description of the preferred embodiments below.

DETAILED DESCRIPTION OF THE PREFERRED EMBODIMENT

The graft of the present invention may be used to plug or occlude any type of fistula, such as the types of fistula illustrated in FIGS. 1 and 2. Other types of fistula that may be occluded by the present invention include, but are not limited to, tracheo-esophageal fistulae, gastro-cutaneous fistulae, or fistulae occuring between the vagina and bladder (vesicovaginal fistulae), between the vagina and urethra (urethrovaginal fistulae), between the anorectum and vagina (rectovaginal fistulae), between the anorectum and bladder (rectovesical fistulae), between the anorectum and urethra (rectourethral fistulae), between the anorectum and prostate (rectoprostatic fistulae) or between any other two portions of the body.

The graft 13 of the present invention may have any suitable configuration. For example, the graft may have a convex configuration, a concave configuration, an S-shaped configuration, a generally straight configuration, or any other configuration capable of being inserted into and secured within a fistula. The graft may be curved to conform to the shape of the fistula, thereby facilitating introduction of the graft, a secure fit of the graft within the fistula, and less discomfort for the patient. A curved configuration makes it easier for the graft to be introduced into the primary opening and directed toward the secondary opening of a curved fistula. Desirably, the graft 13 is an integral unit with a curved, generally conical configuration that tapers from one end having a first diameter D1 to an opposite end having a second diameter D2, where the first diameter D1 is greater than the second diameter D2, as shown in FIG. 3.

Figure 3:
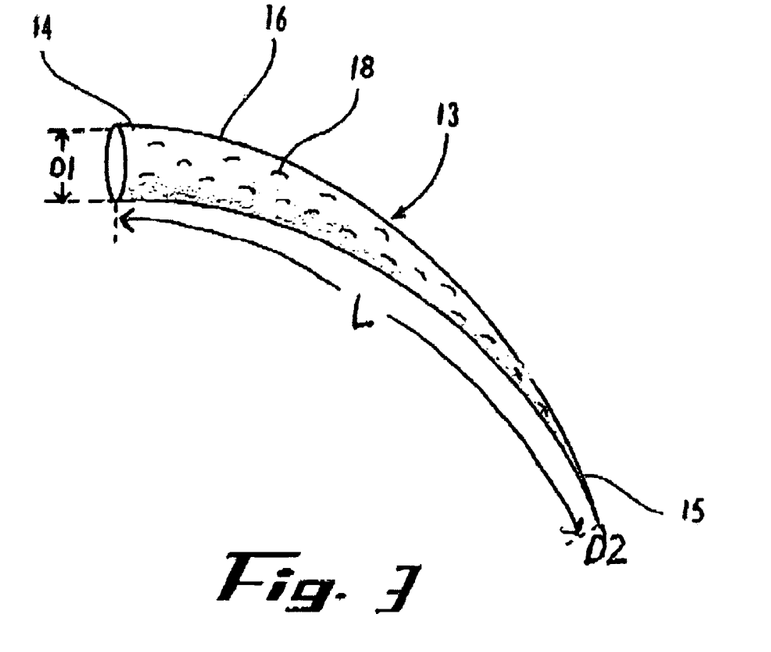
FIG. 3 shows one embodiment of the graft of the present invention.

The graft 13 may have one end with a thicker trumpet-like head 14 and a body 16 that continuously tapers to a thin filamentous tail 15, as shown in FIG. 3. The degree of taper may vary depending on a number of factors, including but not limited to, the diameter of each of the ends (D1 and D2) and the length L of the graft 13.

Although the graft may have any suitable length L, diameter D1, and diameter D2, desirably, the graft 13 has a length L of about 1 to about 15 centimeters, a first diameter D1 of about 1 to about 20 millimeters, and a second diameter D2 of about 0.1 to about 5 millimeters. More desirably, the graft 13 has a length L of about 3 to about 12 centimeters, a first diameter D1 of about 2 to about 15 millimeters, and a second diameter D2 of about 0.5 to about 3.5 millimeters. Even more desirably, the graft has a length L of about 5 to about 10 centimeters, a first diameter D1 of about 5 to about 10 millimeters, and a second diameter D2 of about 1 to about 2 millimeters. The graft of the present invention may be used to close any diameter of primary opening up to the limits of the head diameter D1. By applying adequate force to the graft during insertion, the head 14 of the graft 13 conforms exactly to the size of the primary opening.

The graft 13 of the present invention may be made of any biocompatible material suitable for implantation into a mammalian body. Desirably, the graft 13 is made of a single, non-allergenic biological or synthetic material.

Suitable biological materials that may be used in the present invention include, but are not limited to, tissue from the patient themselves (an autograft), tissue from a human cadaveric donor (an allograft), or tissue from an unrelated animal donor (a heterograft). Desirably, the material promotes angiogenesis and/or site-specific tissue remodeling.

Autograft tissue is grown from a skin biopsy of the patient. Once the fibroblasts have regenerated and formed enough new tissue, the new tissue may be injected back into the surgical site of the same patient. This process takes several weeks to complete; but avoids tissue rejection and disease transmission. One such product is Isolagen (Isolagen Inc.—Houston, Tex.).

Suitable cadaveric materials include, but are not limited to, cadaveric fascia and cadaveric dura matar. Specific suitable cadaveric allografts include, but are not limited to, AlloDerm, (LifeCell Corp.—Branchburg, N.J.), Cymetra, (LifeCell Corp.—Branchburg, N.J.), Dermaloga, Fascion (Fascia Biosystems, LLC—Beverly Hills, Calif.), and Suspend (Mentor—Irving, Tex.). These products are freeze-dried, or lyophilized, acellular dermal tissue from cadaveric donors. Some require reconstitution before implantation. Although disease transmission or antigenic reaction is possible, the risk may be minimized by an extensive screening and processing of the material.

Heterograft materials are taken from a donor of one species and grafted into a recipient of another species. Examples of such materials include, but are not limited to, Surgisis (Cook Surgical—Bloomington, Ind.), Permacol (TSL—Covington, Ga.), Pelvicol (Bard Inc.—Murray Hill, N.J.) and PeriGuard, (Bio-Vascular Inc.—St Paul, Minn.). In one embodiment of the present invention, an injectable heterograft, such as a heterograft of small intestinal submucosa or other material having a viscosity sufficient to prevent the material from running out or being squeezed out of the fistula, is used.

Such biological materials may be rendered non-cellular during processing to avoid immunological rejection. Suitable biological tissues may be implanted in potentially infected surgical fields and resist infection, unlike some synthetic preparations that may elicit a foreign body reaction or act as a nidus for infection.

Desirably, a bioremodelable material is used in the devices and methods of the present invention. More desirably, a bioremodelable collagenous material is used. Bioremodelable collagenous materials can be provided, for example, by collagenous materials isolated from a suitable tissue source from a warm-blooded vertebrate, and especially a mammal. Such isolated collagenous material can be processed so as to have bioremodelable properties and promote cellular invasion and ingrowth and eventual reconstruction of the host tissue itself. Bioremodelable materials may be used in this context to promote cellular growth within the site in which a medical device of the invention is implanted.

Suitable bioremodelable materials can be provided by collagenous extracellular matrix materials (ECMs) possessing biotropic properties. Illustrative suitable extracellular matrix materials for use in the invention include, for instance, submucosa (including for example small intestinal submucosa, stomach submucosa, urinary bladder submucosa, or uterine submucosa, each of these isolated from juvenile or adult animals), renal capsule membrane, dermal collagen, amnion, dura mater, pericardium, serosa, peritoneum or basement membrane materials, including liver basement membrane or epithelial basement membrane materials. These materials may be isolated and used as intact natural forms (e.g. as sheets), or reconstituted collagen layers including collagen derived from these materials and/or other collagenous materials may be used. For additional information as to submucosa materials useful in the present invention, and their isolation and treatment, reference can be made to U.S. Pat. Nos. 4,902,508, 5,554,389, 5,733,337, 5,993,844, 6,206,931, 6,099,567, and 6,331,319. Renal capsule membrane can also be obtained from warm-blooded vertebrates, as described more particularly in International Patent Application serial No. PCT/US02/20499 filed Jun. 28, 2002, published Jan. 9, 2003 as WO03002165.

As prepared and used, the ECM and any other collagenous material used, may optionally retain growth factors or other bioactive components native to the source tissue. For example, submucosa or other ECMs may include one or more growth factors such as basic fibroblast growth factor (FGF-2), transforming growth factor beta (TGF-beta), epidermal growth factor (EGF), and/or platelet derived growth factor (PDGF). As well, submucosa or other ECM when used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the material used for the covering. These non-native bioactive components may be naturally-derived or recombinantly produced proteins that correspond to those natively occurring in an ECM tissue, but perhaps of a different species (e.g. human proteins applied to collagenous ECMs from other animals, such as pigs). The non-native bioactive components may also be drug substances. For example, one drug substance that may be incorporated into and/or onto the covering materials is an antibiotic.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

Suitable synthetic materials that may be used in the present invention include, but are not limited to, polygalactin, polydioxanone, hyaluronic acid, polyglycolic acid, and polyethylene terephthalate. These materials avoid foreign body rejection and may be eventually incorporated into the host tissue.

Desirably, the biological or synthetic material used in the present invention assists in reconstruction of the host tissues, elicits little immunological reaction, and has some inherent resistance to infection. Such material allows incorporation of the graft into the fistula (rather than complete absorption of the graft into the surrounding tissue), thereby occluding the fistula.

In one embodiment of the present invention, a drug, such as an antibiotic, is incorporated into the graft of the present invention, as an extra precaution or means of treating any residual infection within the fistula. The graft may also be used in conjunction with a sealant or sclerosing solution which may be injected into the main fistula tract and any side branches. Several possible sealants are described in the prior art. One of the more commonly used sealants is fibrin glue, known as Tisseal (Baxter Inc.). The glue is prepared by mixing coagulation activation factors with fibrinogen, which react to form fibrin. The fibrin forms a matrix, which acts as a scaffold for tissue ingrowth and results in the sealing of the fistula tract.

The graft 13 of the present invention may be inserted into the fistula by pulling the tail 15 of the graft 13 through the primary opening 2 of the fistula and towards the secondary opening 3. This may be accomplished by using, for example, a pair of surgical hemostats or a fistula probe or scope, which is passed through the secondary opening 3 and out through the primary opening 2. The tail 15 of the graft 13 may then be grasped by the hemostats, or secured to the probe or scope, and withdrawn retrograde into the fistula. As the graft 13 is being withdrawn through the fistula, the head 14 of the graft 13 may be gradually "wedged" into the primary opening 2 causing the graft 13 to become lodged in place so that it does not fall out or exude, as with the fibrin glue technique.

To assist in anchoring the graft within the fistula, the outer surface of the graft may contain protrusions 18 that interact with the fistula. Anorectal fistulae pass through the cylindrical, well-defined internal sphincter muscle 6 containing an almost rigid hole, which is the narrowest point along the fistula tract. Desirably, the protrusions on the graft are adapted to be pulled through the hole and wedged against the distal portion of the hole to further anchor the graft.

In an alternative embodiment of the present invention, either end of the graft or both ends of the graft are secured by sutures and trimmed to avoid either end from protruding excessively from the fistula tract after the procedure. The suture may be formed as an integral part of the graft or as a separate component.

In another embodiment, the graft is anchored within the fistula by threading a securing device having a central lumen, over the tail of the graft and securing it into position at skin level (e.g., by crimping it). In yet another embodiment, further anchoring of the graft is achieved by using a material such as a small intestinal submucosa heterograft (a freeze-dried material that requires rehydration before use) for the graft and inserting the graft into the tract before the graft material has been fully expanded by hydration. Any other suitable means of securement, such as introducing adhesive into the fistula tract, may also be used to anchor the graft within the fistula.

In one embodiment, antologous fibrin glue is used in conjunction with the fistula graft to supplement the adhesive and occlusive properties of the disclosed invention. This involves the use of an autologous composite of platelets and growth factors derived from the patient's own blood. (Symphony PCS, DePuy AcroMed Inc.). The composite may be derived from a fresh sample of blood drawn from the patient at the time of surgery. The blood may then be centrifuged, and the platelets, which contain growth factors such as epidermal growth factor (EGF) and transforming growth factor-beta (TGFβ), harvested. Having centrifuged the blood, retrieved the platelet "pellet" and prepared the composite, the sealant may then be injected into the fistula tract(s) to help maintain the graft in place.

Closure of a fistula tract may be performed as a one-stage or two-stage procedure. As a one-stage procedure, the fistula tract is closed or sealed at the same time as the initial surgery. The advantage of this method is that it avoids a second operation and minimizes expense and inconvenience. The main disadvantage is that immediate implantation of the graft into an "unprepared" and possibly infected fistula tract may result in secondary infection of the graft. As a two-stage procedure, a seton is first placed through the fistula tract to allow mechanical drainage of the fistula tract. Several weeks later, the seton is removed and the graft is inserted into the fistula.

An alternative methodology involves preliminary endoscopic visualization (fistuloscopy) and "cleaning" of the fistula tract, as disclosed in co-pending application Ser. No. 10/945,634 (Armstrong). This procedure may be performed by a very thin flexible endoscope, which is inserted into the secondary opening of the fistula tract, and advanced under direct vision through the fistula tract and out the primary opening. By performing preliminary fistuloscopy of the fistula tracts, the primary opening is accurately identified and the tracts are "cleaned out" by means of an irrigating fluid. Any inflammatory or necrotic tissue within the tract is therefore removed, prior to inserting the graft. The tail of the graft may be attached to the fistuloscope, which may then be withdrawn through the fistula tract so that the graft gets wedged in place, as described above.

Figure 4:
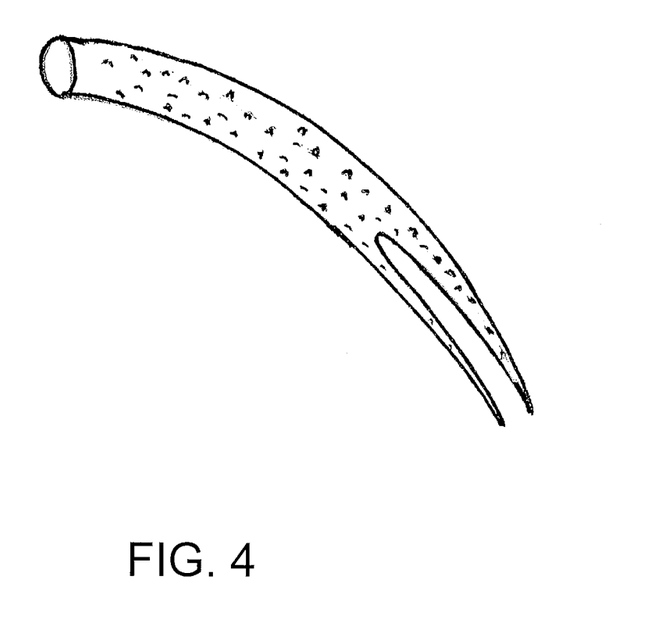
FIG. 4 shows another embodiment of the graft of the present invention.

For multiple fistula, multiple grafts may be inserted until all fistula tracts have been closed. In the case of a complex fistula, for instance the horseshoe fistula, there may be one primary opening and two or more tracts leading from that opening. In this instance, a graft may be configured with one "head" component (larger diameter end), and two "tails" (smaller diameter ends). FIG. 4 illustrates an embodiment of such a graft. Desirably, accurate identification of all fistula tracts and the primary opening is facilitated by first performing fistuloscopy. Once the entire tract has been identified and cleaned out, each tail may be pulled through the primary opening into each fistula in turn, desirably using a fistuloscope or an instrument passed through the instrument channel of a scope. Adequate force may be applied to the tail to ensure that the head of the graft is firmly secured in the primary opening. The head of the graft and/or each of the tails may be further secured by any of the methods described above.

The success of the present invention was demonstrated in a clinical trial evaluating the efficacy of a biodegradable lyophilized porcine submucosa plug, as compared to the fibrin glue technique, in closing anorectal fistulae. Thirteen of fifteen patents (87%) treated with the plug had complete closure of all fistula tracts, whereas only four of ten (40%) patents treated with the fibrin glue technique had complete closure.

It is intended that the foregoing detailed description be regarded as illustrative rather than limiting, and that it be understood that it is the following claims, including all equivalents, that are intended to define the spirit and scope of this invention.

The invention claimed is:

1. A method of treating an anorectal fistula of a human patient, the anorectal fistula having a tract extending from a primary opening positioned in the anorectum at the dentate line to a secondary opening, wherein the secondary opening is positioned outside the anorectum in the perianal skin, the method comprising
   inserting a plug from the anorectum into the primary opening of the tract so as to occlude said primary opening, wherein the plug comprises a taper between a first plug end and a second plug end, wherein the plug comprises bioremodelable material that promotes cellular invasion and ingrowth and reconstruction of host tissue within the plug, and wherein the bioremodelable material is selected from the group consisting of a cadaveric material from a human donor and a heterograft material from a non-human donor, and
   positioning the plug in the tract whereby the bioremodelable material extends along the fistula tract from the primary opening to the secondary opening and promotes cellular invasion and ingrowth and reconstruction of host tissue within the plug.

2. The method of claim 1, wherein the bioremodelable material comprises dermal collagen.

3. The method of claim 2, wherein the bioremodelable material comprises submucosa.

4. The method of claim 1, wherein the plug incorporates a drug.

5. The method of claim 1, wherein the plug incorporates an antibiotic agent.

6. The method of claim 1, wherein the bioremodelable material comprises an intact acellular sheet of dermal collagen or submucosa.

7. The method of claim 1, wherein said inserting comprises pulling said plug through the primary opening towards the secondary opening whereby wedging the plug into the primary opening.

8. The method of claim 1, further comprising securing an end of the plug adjacent the primary opening to tissue of the patient.

9. The method of claim 1, further comprising cutting portions of the plug extending from at least one of the primary opening and the secondary opening of the fistula after placement of the plug in the fistula.

10. The method of claim 1, wherein the anorectal fistula comprises two or more tracts leading from the primary opening and the second plug end comprises a first tail and a second tail, the inserting comprising placing the first tail into a first tract and inserting the second tail into a second tract.

11. A method for treating an anorectal fistula of a patient, the fistula having a tract extending from a primary opening positioned in the anorectum at the dentate line to a secondary opening, wherein the secondary opening is positioned outside the anorectum in the perianal skin, the method comprising:

inserting a plug into the primary opening of the fistula so as to occlude the primary opening, wherein the plug comprises a generally conical body having a first end with a first diameter and a second end with a second diameter that is smaller than the first diameter, wherein the plug comprises bioremodelable material selected from the group consisting of a cadaveric material from a human donor and a heterograft material from a non-human donor, positioning the plug in the tract whereby the bioremodelable material extends along the fistula tract from the primary opening to the secondary opening of the fistula and promotes cellular invasion and ingrowth and reconstruction of host tissue within the plug; and securing an end of the plug to tissue of the patient, wherein the end is adjacent the primary opening or secondary opening.

12. The method of claim 11, wherein:

said implanting includes positioning the second end of the plug adjacent the primary opening and pulling the plug into the fistula tract through the primary opening, whereby wedging the first end of the plug into the primary opening; and said securing includes securing an end of the plug adjacent the primary opening to tissue of the patient.

13. The method of claim 11, wherein the securing comprises the application of an adhesive.

14. The method of claim 11, the bioremodelable material comprises an intact acellular sheet of dermal collagen or submucosa.

15. The method of claim 11, wherein the securing an end of the plug to tissue of the patient comprises suturing an end of the plug to tissue of the patient adjacent the primary opening or the secondary opening.

16. The method of claim 11, wherein the bioremodelable material incorporates a drug.

17. A method for treating a fistula of a patient, the fistula having a tract extending from a primary opening in a first body lumen to a secondary opening in a second body lumen, the method comprising:

implanting a plug in the fistula tract so as to occlude the primary opening, the plug having a plug body, wherein the plug body is tapered and comprises bioremodelable material selected from the group consisting of a cadaveric material from a human donor and a heterograft material from a non-human donor, wherein the bioremodelable material extends along the fistula tract from the primary opening to the secondary opening of the fistula; and securing the plug to tissue of the patient, wherein the securing comprises the application of an adhesive, and cutting a portion of the plug body extending from at least one of the primary opening and the secondary opening of the fistula.

18. The method of claim 17, wherein the bioremodelable material comprises an intact, acellular sheet of dermal collagen or submucosa.

19. The method of claim 17, wherein the securing an end of the plug to tissue of the patient comprises suturing an end of the plug to tissue of the patient, wherein said end is adjacent the primary opening or the secondary opening.

20. The method of claim 17, wherein the bioremodelable material incorporates a drug.

* * * * *

UNITED STATES PATENT AND TRADEMARK OFFICE
CERTIFICATE OF CORRECTION

| | | |
|---|---|---|
| PATENT NO. | : 8,764,791 B2 | Page 1 of 1 |
| APPLICATION NO. | : 11/807801 | |
| DATED | : July 1, 2014 | |
| INVENTOR(S) | : Armstrong | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 891 days.

Signed and Sealed this
Twenty-fifth Day of August, 2015

Michelle K. Lee
*Director of the United States Patent and Trademark Office*